(12) United States Patent
Grieu et al.

(10) Patent No.: US 8,650,957 B2
(45) Date of Patent: Feb. 18, 2014

(54) METHOD OF EVALUATING THE AGEING OF AN ELECTRONIC ASSEMBLY

(75) Inventors: Marc Grieu, Ivry sur Seine (FR); Gregor Massiot, Toulouse (FR)

(73) Assignee: European Aeronautic Defence and Space Company Eads France, Paris (FR)

( * ) Notice: Subject to any disclaimer, the term of this patent is extended or adjusted under 35 U.S.C. 154(b) by 419 days.

(21) Appl. No.: 13/129,416

(22) PCT Filed: Nov. 16, 2009

(86) PCT No.: PCT/FR2009/052189
§ 371 (c)(1),
(2), (4) Date: Jun. 7, 2011

(87) PCT Pub. No.: WO2010/055272
PCT Pub. Date: May 20, 2010

(65) Prior Publication Data
US 2011/0271761 A1 Nov. 10, 2011

(30) Foreign Application Priority Data
Nov. 17, 2008 (FR) ..................................... 08 57792

(51) Int. Cl.
*G01N 3/32* (2006.01)
(52) U.S. Cl.
USPC .......................................................... 73/577
(58) Field of Classification Search
USPC ................................ 73/577, 788, 808; 702/34
See application file for complete search history.

(56) References Cited

U.S. PATENT DOCUMENTS

| | | | | |
|---|---|---|---|---|
| 5,958,556 | A * | 9/1999 | McCutcheon | 428/172 |
| 6,704,664 | B2 * | 3/2004 | Su et al. | 702/34 |
| 7,260,509 | B1 * | 8/2007 | Brand et al. | 703/2 |
| 7,904,202 | B2 * | 3/2011 | Hoppe | 700/245 |
| 7,974,791 | B2 * | 7/2011 | Broddegaard et al. | 702/35 |
| 2008/0275672 | A1 | 11/2008 | Varon-Weinryb | |

FOREIGN PATENT DOCUMENTS

| | | | |
|---|---|---|---|
| SU | 1738378 | * | 7/1992 |
| WO | WO 2007/102155 | | 9/2007 |

OTHER PUBLICATIONS

Lall et al., "Failure-Envelope Approach to Modeling Shock and Vibration Survivability of Electronic and MEMS packaging," 2005 Electronic Components and Technology Conference, May 31, 2005, pp. 480-490, IEEE, Piscataway, NJ,USA.
Wang et al, "Modified highly accelerated life test for aerospace electronics," ITHERM 2002 Intersociety Conference on Thermal and Thermomechanical Phenomena in Electronic Systems, San Diego, CA, May 30, 2002, pp. 940-945, vol. conf. 8, New York, NY, USA.

(Continued)

*Primary Examiner* — J M Saint Surin
(74) *Attorney, Agent, or Firm* — IM IP Law PLLC; C. Andrew Im

(57) ABSTRACT

To measure the fatigue ageing of an electronic component in an electronic assembly subjected to mechanical excitations, a dynamic correspondence is established between kinematic measurements at certain points and mechanical stresses experienced at points that are critical as regard to the reliability of the electronic assembly. The critical points may be different from the measurement points. This correspondence is integrated into a monitoring device as a functionality that calculates the mechanical stresses, thereby providing an indicator of the cumulative fatigue damage. The invention is such that the monitoring device can be incorporated into the electronic assembly, preferably, the monitoring device is autonomous both as regard to processing the measurements and calculating the damage.

9 Claims, 1 Drawing Sheet

(56) References Cited

OTHER PUBLICATIONS

Przemyslaw et al., "Application of FPGA units in combined temperature cycle and vibration reliability tests of lead-free interconnections," Electronics System Integration Technology Conference, Sep. 1, 2008, pp. 1375-1380, IEEE, Piscataway, NJ, USA.

X. Moreau, "La dérivation non entière en isolation vibratoire et son application dans le doamine de l'automobile. La suspension CRONE du concept à la réalisation", PhD thesis, Bordeaux 1 University, 1995.

Grieu et al., "Durability Modelling of a BGA Component under Random Vibration," $9^{th}$ Int. Conf. on Thermal, Mechanical and Multi-Physics Simulation Experiments in Microelectronics and Micro-Systems, Apr. 20-23, 2008, pp. 1-8.

Lemaître et al, "Mécanique des matériaux solides", Dunod, $2^{nd}$ Edition, Jun. 1, 2004.

Fatigue sous sollicitations d'amplitude variable. Méthode Rainflow de comptage des cycles, Norme AFNOR A 03-406, Nov. 1993.

* cited by examiner

METHOD OF EVALUATING THE AGEING OF AN ELECTRONIC ASSEMBLY

RELATED APPLICATIONS

This application is a §371 application from PCT/FR2009/052189 filed Nov. 16, 2009, which claims priority from French Patent Application No. 08 57792 filed Nov. 17, 2008, each of which is herein incorporated by reference in its entirety.

TECHNICAL FIELD OF THE INVENTION

The invention relates to a method for evaluating the ageing condition, called vibration fatigue damage, in any electronic system. These may be individual electronic cards or an electronic card assembly. The evaluation is based on a device that measures and digitally processes physical dimensions relating to the stress that is causing the damage.

BACKGROUND OF THE INVENTION

Similar devices currently exist for mechanical parts and structures, but they lack certain features that are needed in order to be applied to electronic cards. These features are the ability to perform real time processing autonomously with the full capacity of an incorporated calculation, the damage estimate having no recourse to telemetry or post-processing.

Telemetry and post-processing of data are currently used to monitor aerostructures and works of art, but the corresponding devices do not simultaneously respond to the criteria of incorporability and autonomy with regard to the calculation.

OBJECT AND SUMMARY OF THE INVENTION

The invention is based on one or more kinematic vibration sensors positioned at specific points, a state observer to dynamically evaluate mechanical stresses at critical points, and a damage calculation at these critical points, with all three being integrated into a device that is embedded and autonomous in terms of function. The specific measurement points and critical damage calculation points are separate or combined, depending on the application.

The concept of a state observer is defined in the fields of automation and information theory. It applies to dynamic systems represented by size dimensions. When a system state is not accessible to measurement, a dynamic model is built to reconstruct the unmeasureable state from other accessible size measurements. This dynamic model is called a dimension state observer. However, constructing a state observer is not always possible, and the ability to construct one is called the observability condition of the dimension.

In this invention, kinematic dimensions (acceleration, velocity, position, or strain) of specific points on the electronic assembly to be monitored are accessible for measurement using sensors, such as accelerometers. In contrast, mechanical stress and even damage states at critical points of the electronic assembly are almost always inaccessible for measurements, except in a laboratory. A state observer for mechanical stress at critical points using measurements of one or more kinematic dimensions and specific points can be established, subject to observability. The observability of mechanical stress depends directly on the specific points where the kinematic sensors are placed. In general, it is sufficient to place the kinematic sensors away from vibration nodes or to place them, for example, on the electronic assembly attachment.

The need to know how to correctly evaluate vibration damage on embedded electronic cards is more and more pronounced. This need relates to a certain number of critical points on these electronic cards, to which submission to vibrations is likely to cause a failure in the electronic assembly. For example, critical points to monitor are solder joints for certain electronic components. In the case of such electronic cards, there are existing monitoring systems included. They can be equipped with accelerometers or strain gauges to measure accelerations or strains to which the card is submitted. However, these sensors can almost never be placed at critical points on the card due to the very small dimensions of the components and even the solder joints. Existing systems therefore cannot access data for the mechanical stress on these critical points. We can measure the card's general ageing condition, but we cannot measure the local fatigue condition of a component, without being able to use a sensor to provide information on the stress applied to the component.

Methods have been proposed by the CALCE (Center for Advanced Life Cycle Engineering) laboratory to make the connection between measurement and stress at critical points. But the major shortcoming of these methods is not taking into account the dynamic effects of vibrations. In fact, the method proposed by the CALCE ignores the majority of methods specific to vibration and relies only on static curvature calculations.

In contrast, this invention relies on state observations that reflect dynamic effects associated with forces of inertia and methods specific to vibration for the electronic assembly. The system proposed by the invention uses kinematic measurements much more broadly to evaluate mechanical stress at critical points as accurately as possible. The multi-axial nature of mechanical stress and the dynamic of the electronic assembly are respected. The advantage of accurately evaluating these mechanical stresses is to be able to much more accurately calculate the damage suffered by the electronic assembly where the critical components are located. Using such a device can improve maintenance forecasts because the indication of damage it provides is used to anticipate potential failures. The proposed approach can apply the principles of monitoring mechanical structures and the digital processing of measurements to know the damage condition at multiple locations, using an embedded device with one or more sensors.

The device integrating the full method is a small embedded electronic monitoring system (PHM for Prognostics and Health Management) with one or more kinematic sensors (acceleration, velocity, position, or strain) and a calculation unit. The monitoring system is designed to estimate the damage caused by a potential failure of the electronic cards constituting the electronic assembly to be monitored. The sensor(s) measure a kinematic dimension at one or respectively more points on the electronic assembly to be monitored. One of the functions of the monitoring system is to evaluate the mechanical stress of vibration, which is the source of a potential failure, from the measurement(s) of the sensor(s). This function is performed by a state observer that can reconstruct the dynamic of the mechanical stress from a dynamic model and kinematic measurements. The function operates in real time. The point(s) of measurement and the point(s) of evaluation for the stress are not necessarily the same. Using a state observer requires only a rather limited unit computing power, and the full device can then be built around a simple microcontroller, for example. Therefore, the same method of evaluating fatigue ageing can be used for integration in a small embedded device with autonomous calculation capacity.

In practice, the state observer can be achieved, for example, by convoluting the acceleration measured with an impulse response in mechanical stress. This way, the entire requested frequency band is taken into account, thereby restoring all dynamic effects. Also, the multi-axial character of the mechanical stress is respected once we use an impulse response for each of the components of the stress tensor. The state observer may be achieved otherwise than by a convolution operation, such as with a differential equation resolution or even by using a non-integer derived model (Xavier Moreau doctoral thesis, No. 95BOR10512, 1995).

The damage estimate is based on the mechanical stress given by the state observer. For example, the damage estimate can be determined by a rainflow count (described in the NF-A03-406 standard "Fatigue sous sollicitations d'amplitude variable, méthode rainflow de comptage des cycles", November 1993, ISSN 0035-3931) and by applying the Palmgren-Miner rule. The required computing power for these operations is very low, which also allows for integration into an embedded device with an autonomous calculation capacity.

The invention therefore relates to a method of evaluating the ageing of an electronic assembly, typically an electronic card, subject to vibratory movement, a method in which:
- one or more kinematic dimensions are measured, such as acceleration or stress, along with one or more specific points subject to vibratory movement, such as the location(s) of attachment to one or more holders,
- a dynamic model is established, relating the kinematic dimensions measured and the mechanical stress suffered at critical points with regard to vibration fatigue, this model being called a state observer,
- mechanical stress calculated based on the state observer is used to deduce a damage condition for each of the critical points, damage conditions characterizing the ageing to be determined,
- kinematic measurements, a state observer, and damage state calculations are included in an embedded device having an autonomous calculation capacity.

BRIEF DESCRIPTION OF THE DRAWINGS

The invention will be better understood upon reading the following description and studying the figures that accompany it. They are presented for illustrative purposes only and are not limiting to the invention. The figures show.

DETAILED DESCRIPTION OF THE EMBODIMENTS

Figure 1:
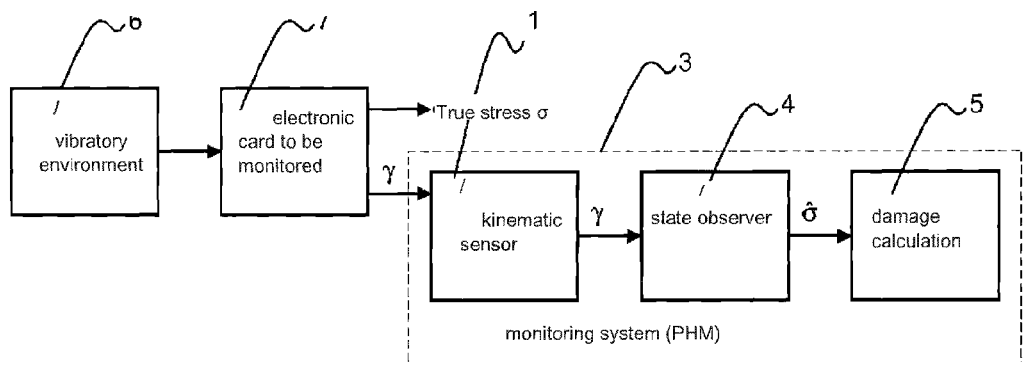
FIG. 1 is a schematic diagram of the method of the invention.

FIG. 1 shows that an electronic assembly, such as an electronic card 7, is subject by an environment 6 to mechanical vibrations. According to the invention, the monitoring system, and therefore the ageing evaluation, is implemented using a system 3 comprising a kinematic sensor 1, a function called a state observer 4 that processes the γ signals produced by the sensor 1 to return an estimate $\hat{\sigma}$ of the true mechanical stress σ on a critical point on the assembly 7, and a function 5 to calculate the cumulative fatigue damage at this critical point of the assembly 7 taking as a variable the results $\hat{\sigma}$ produced by the state observer 4. The state observer 4 is capable of simulating the consequences of excitation of the environment 6 at a chosen location while the sensor 1 is located at another location.

Figure 2:
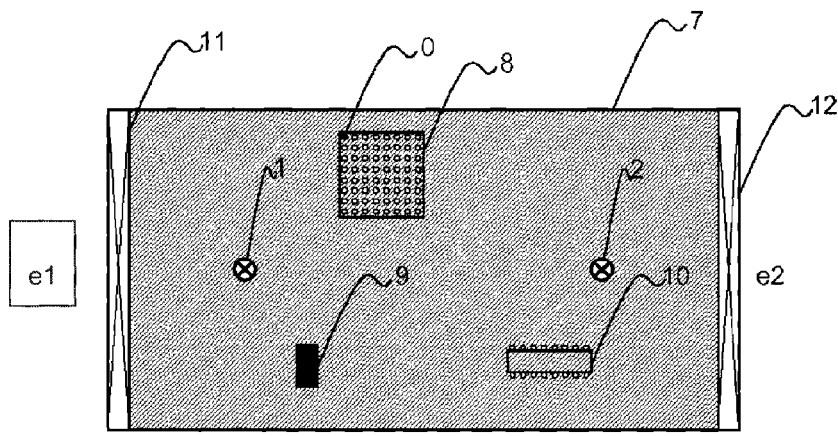
FIG. 2 is a practical example of using the invention.

For example, FIG. 2, the assembly 7 is an electronic card equipped with useful components 8 to 10, particularly critical components in the sense that their functionality must be guaranteed, and therefore monitored, and sensitive in the sense that vibrations are likely to cause a failure. The card 7 is attached to its holder by attachments such as 11 to 12. Sensors 1 to 2, accelerometers here, measure the effects of excitations e1 to e2 applied to the attachments 11 to 12. According to the invention, with the state observer 4, we can evaluate the mechanical stress at the locations on the card 7 where the components 8 to 10 are placed.

To simplify the explanation, note that excitations e1 to e2 are oriented in the same direction, perpendicular to the card 7, but they are not necessarily synchronous. However, it would be possible to construct a state observer even if this obligation were not satisfied, but the vibrations according to the directions in the plane of the card 7 cause strains with much less magnitude, which cause less damage to the electronic components. In principle, it is the holder that vibrates and transmits its vibrations to the card by attachments 11 to 12. In one example, the vibration perpendicular to the card 7 predominantly leads to tensile/compression stress, or normal stress, on the solder joints 0 of a critical electronic component 8 (BGA, Bail Grid Array) which potentially leads to a tensile/compression rupture in this joint and a failure of the electronic card 7. In the invention, particularly if the accelerometer is a three-dimensional accelerometer, we can calculate the damage resulting from the three directions at all time.

To simplify the explanation, we will also note that the electronic assembly 7 responds linearly to the vibratory excitations. This means that any physical dimension relating to the vibration behaves additively when several applied vibration excitations are superimposed at different or combined locations. This restriction is not limiting because nearly all of the electronic assembles behave as such in practice.

A state observer for the tensile/compression stress σ at critical point 0 is achieved for example by a convolution operation between the acceleration measurements $\gamma_1$ and $\gamma_2$ from specific points, and impulse responses $s_1$ et $s_2$, whose determination is specified later. The convolution operation achieving the state observer is written as:

$$\hat{\sigma}(t) = \sum_{k=0}^{n-1} s_1(k\tau)\gamma_1(t-k\tau) + \sum_{k=0}^{n-1} s_2(k\tau)\gamma_2(t-k\tau)$$

n being a number of necessary and sufficient points to represent impulse responses $s_1$ and $s_2$, k being an integer successively representing all of the values from 0 to n−1, τ being a sampling time interval of kinematic measurements, and noting $\hat{\sigma}(t)$ the normal stress evaluated at critical point 0 at the present incident t, $\gamma_4(t-k\tau)$ the k-th last measured value of $\gamma_1$ following the sampling at time interval τ, $\gamma_2(t-k\tau)$ the k-th last measured value of $\gamma_2$ following the sampling at time interval τ, $s_1(k\tau)$ the k-th tabulated value of the impulse response $s_1$ according to the sampling at time interval τ, $s_2(k\tau)$ the k-th tabulated value of the impulse response $s_2$ according to the sampling at time interval τ, and using the well-known notation Σ designating a discrete summation according to a discrete variable whose endpoints are indicated in the subscript and superscript of the letter. The variable indicating the present time t is itself sampled at time interval τ and therefore takes the discrete multiple values of τ. The observer presented here therefore delivers at each instant t multiple of τ an estimate $\hat{\tau}$ of the true mechanical stress σ at critical point 0 whose direct measurement is almost always impossible.

Figure 3:
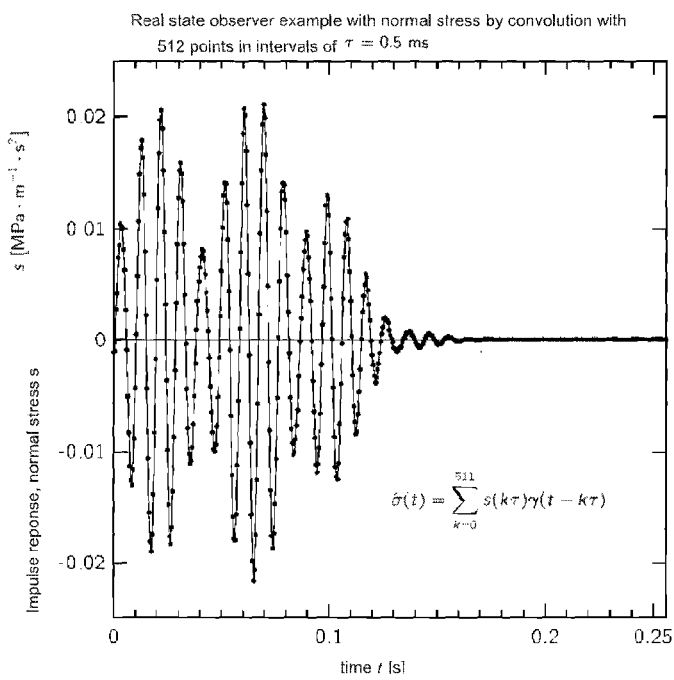
FIG. 3 is an example of a state observer with a mechanical stress for a brazed joint on a critical electronic component, based on an actual case.

FIG. 3 shows an example of a state observer in the form of a convolution taken from the study of an actual electronic card. In this example, there is only one vibratory excitation e1 that synchronously applies to all of the card's attachment points in the direction perpendicular to the plane of the card. This excitation is therefore characterized by a number of degrees of freedom equal to 1. A single kinematic sensor is necessary and sufficient to construct a state observer for each component of the stress tensor by a critical point, subject to observability of the positions respective of the sensor, the critical point, and the characteristics of the sensor. In the sample in FIG. 3, the kinematic sensor is an accelerometer that measures the acceleration γ perpendicular to the plane of the card, and the evaluated mechanical stress $\hat{\sigma}$ is the normal stress in a brazed joint on an electronic component of BGA type. In this example, the number n of points representing the impulse response is 512, the time interval is τ=0.5 ms and therefore the convolution is based on a time range of 0.256 s. The vibration of the electronic card is taken into account for a frequency range from 0 Hz to 1000 Hz, given the sampling time interval τ=0.5 ms. In this example taken from an actual case, the number of arithmetic operations to be performed per second by the calculation unit of the monitoring device (PHM) for the state observer function for critical point 0 is 1,024,000 multiplications per second and 1,024,000 additions per second. The required calculation capacity for the state observer function is therefore quite modest, based on current electronic architectures. The device completely bypasses any post-processing or telemetry, because the calculation technique used provides the result at the cost of a limited and rather low number of calculations.

We can note that the number of sensors required must generally be greater than or equal to the number of degrees of freedom of excitation. If the sensor number is less, the observability condition is generally not verified. This highlights the example given in FIG. 2 with two kinematic sensors 1 and 2 for two independent vibratory excitations e1 and e2.

As previously stated, an example of determining the impulse responses $s_1$ and $s_2$ is given below for the example in FIG. 2. In the following, each dimension with a tilde (~) designates the Fourier transform of a time dimension. The pulsation, which is the variable for a Fourier transform, is denoted by ω and is homogenous to the inverse of a time. The unit ω is usually the radian per second.

Thus, the function $\tilde{\gamma}_1(\omega)$ results from the Fourier transformation of the function $\gamma_1(t)$, acceleration delivered by the sensor 1. Function $\tilde{\gamma}_2(\omega)$ results from the Fourier transformation of the function $\gamma_2(t)$, acceleration delivered by the sensor 2. The function $\tilde{e}_1(\omega)$ results from the Fourier transformation of the function $e_1(t)$, excitation applying to the attachment 11. The function $\tilde{e}_2(\omega)$ results from the Fourier transformation of the function $e_2(t)$, excitation applying to the attachment 12. The function $\tilde{\sigma}_0(\omega)$ results from the Fourier transformation of the function $\sigma_0(t)$ mechanical stress at the critical point 0. Note that the Fourier transforms are complex scalar dimensions.

Four functions $H_{11}(\omega)$, $H_{12}(\omega)$, $H_{21}(\omega)$, $H_{22}(\omega)$, of the pulsation ω are each defined as the response of one of the measurement points in terms of acceleration, at a pulsation unit excitation ω at one of the excitation points, all other excitations being maintained identically as null. By the linearity specified above, these functions are generally written as the ratio of an acceleration on a non-null excitation which is the cause, the other excitations being maintained identically as null. This ratio is independently the excitation applied due to the linearity specified above. Explicitly:

$$H_{11}(\omega) = \frac{\tilde{\gamma}_1(\omega)}{\tilde{e}_1(\omega)}\bigg|_{e_1=0}$$

$$H_{21}(\omega) = \frac{\tilde{\gamma}_2(\omega)}{\tilde{e}_1(\omega)}\bigg|_{e_2=0}$$

The subscript notation $e_2=0$ means that the ratio is calculated for the excitation e1 applied alone.

$$H_{12}(\omega) = \frac{\tilde{\gamma}_1(\omega)}{\tilde{e}_2(\omega)}\bigg|_{e_1=0}$$

$$H_{22}(\omega) = \frac{\tilde{\gamma}_2(\omega)}{\tilde{e}_2(\omega)}\bigg|_{e_2=0}$$

The subscript notation $e_1=0$ means that the ratio is calculated for the excitation e2 applied alone.

These four functions are independent of the excitations applied. They can be determined experimentally, for example by proceeding successively through the unit excitations indicated above, by successively scanning the pulsation values ω. The finite elements method, a very common and recognized calculation technique in the industry, civil engineering, and science, also offers multiple means for determining these four functions, such as by numerically calculating the experimental procedure that can determine these four functions.

Similarly, two functions $G_1(\omega)$ and $G_2(\omega)$ for pulsation ω are each defined as the response for critical point 0 in terms of mechanical stress, at a unit pulsation excitation ω at one of the excitation points, all other excitations being maintained identically null. By linearity, like before:

$$G_1(\omega) = \frac{\tilde{\sigma}_0(\omega)}{\tilde{e}_1(\omega)}\bigg|_{e_2=0}$$

$$G_2(\omega) = \frac{\tilde{\sigma}_0(\omega)}{\tilde{e}_1(\omega)}\bigg|_{e_1=0}$$

The subscript notation $e_1=0$ or $e_2=0$ means that the ratio is calculated for an excitation applied alone. The two functions G1 and G2 can be determined experimentally or by the finite element method, as for the four previous functions.

The Fourier transforms $\tilde{\gamma}_1(\omega)$ and $\tilde{\gamma}_2(\omega)$ of the two accelerations $\gamma_1(t)$ and $\gamma_2(t)$ measured by the sensors 1 and 2 are written by linearly superposing the responses to the two excitations e1 and e2:

$$\begin{cases} \tilde{\gamma}_1(\omega) = H_{11}(\omega)\tilde{e}_1(\omega) + H_{12}(\omega)\tilde{e}_2(\omega) \\ \tilde{\gamma}_2(\omega) = H_{21}(\omega)\tilde{e}_1(\omega) + H_{22}(\omega)\tilde{e}_2(\omega) \end{cases}$$

This scalar system is written in matrix form:

$$\begin{pmatrix} \tilde{\gamma}_1(\omega) \\ \tilde{\gamma}_2(\omega) \end{pmatrix} = \begin{pmatrix} H_{11}(\omega) & H_{12}(\omega) \\ H_{21}(\omega) & H_{22}(\omega) \end{pmatrix} \begin{pmatrix} \tilde{e}_1(\omega) \\ \tilde{e}_2(\omega) \end{pmatrix}$$

The reverse matrix system is written:

$$\begin{pmatrix} \tilde{e}_1(\omega) \\ \tilde{e}_2(\omega) \end{pmatrix} = \begin{pmatrix} H_{11}(\omega) & H_{12}(\omega) \\ H_{21}(\omega) & H_{22}(\omega) \end{pmatrix}^{-1} \begin{pmatrix} \tilde{\gamma}_1(\omega) \\ \tilde{\gamma}_2(\omega) \end{pmatrix}$$

where the superscript −1 indicates the reverse of the matrix. Or, in scalar system form:

$$\begin{cases} \tilde{e}_1(\omega) = \dfrac{H_{22}(\omega)\tilde{\gamma}_1(\omega) - H_{12}(\omega)\tilde{\gamma}_2(\omega)}{H_{11}(\omega)H_{22}(\omega) - H_{12}(\omega)H_{21}(\omega)} \\ \tilde{e}_2(\omega) = \dfrac{-H_{21}(\omega)\tilde{\gamma}_1(\omega) + H_{11}(\omega)\tilde{\gamma}_2(\omega)}{H_{11}(\omega)H_{22}(\omega) - H_{12}(\omega)H_{21}(\omega)} \end{cases}$$

The Fourier transform $\tilde{\sigma}_0(\omega)$ of the mechanical stress $\sigma_0$ at the critical point 0 is written by linearly superposing the responses to the two excitations $e_1$ and $e_2$:

$$\tilde{\sigma}_0(\omega) = G_1(\omega)\tilde{e}_1(\omega) + G_2(\omega)\tilde{e}_2(\omega)$$

This expression is then written according to the Fourier transforms of the accelerations:

$$\tilde{\sigma}_0(\omega) = \frac{G_1(\omega)H_{22}(\omega) - G_2(\omega)H_{21}(\omega)}{H_{11}(\omega)H_{22}(\omega) - H_{12}(\omega)H_{21}(\omega)} \tilde{\gamma}_1(\omega) + \frac{-G_1(\omega)H_{12}(\omega) + G_2(\omega)H_{11}(\omega)}{H_{11}(\omega)H_{22}(\omega) - H_{12}(\omega)H_{21}(\omega)} \tilde{\gamma}_2(\omega)$$

We then define the two factors $\tilde{\gamma}_1(\omega)$, respectively $\tilde{\gamma}_2(\omega)$ in the expression above as two functions $\tilde{s}_1(\omega)$ and respectively $\tilde{\gamma}_2(\omega)$:

$$\tilde{s}_1(\omega) = \frac{G_1(\omega)H_{22}(\omega) - G_2(\omega)H_{21}(\omega)}{H_{11}(\omega)H_{22}(\omega) - H_{12}(\omega)H_{21}(\omega)}$$

$$\tilde{s}_2(\omega) = \frac{-G_1(\omega)H_{12}(\omega) + G_2(\omega)H_{11}(\omega)}{H_{11}(\omega)H_{22}(\omega) - H_{12}(\omega)H_{21}(\omega)}$$

The impulse responses $s_1(t)$ and $s_2(t)$ are simply the reverse Fourier transforms of $\tilde{s}_1(\omega)$ of $\tilde{s}_2(\omega)$ respectively. Note that $s_1(t)$ and $s_2(t)$ are actual scalar dimensions, by their physical nature. There is an algebraic reason for the properties of the Fourier transformation. $s_1(t)$ and $s_2(t)$ are the two functions that, convoluted respectively with the measurements $\gamma_1(t)$ and $\gamma_2(t)$, return the mechanical stress $\sigma_0(t)$ at the critical point 0 for the electronic assembly 7:

$$\sigma_0(t) = \int_0^t s_1(u)\gamma_1(t-u)du + \int_0^t s_2(u)\gamma_2(t-u)du$$

The variable u below the integral sign is the dummy integration variable.

A discretized version of this integral equation is the expression given above the state observer $\hat{\sigma}(t)$. To obtain such a discretized version, the integrals are replaced by discrete summations and only the values $s_1$ et $s_2$, are used, taken at multiple points of the time interval $\tau$:

$$\hat{\sigma}(t) = \sum_{k=0}^{n-1} s_1(k\tau)\gamma_1(t-k\tau) + \sum_{k=0}^{n-1} s_2(k\tau)\gamma_2(t-k\tau)$$

Discretization is valid only with a small enough time interval to properly represent the integrals and responses $s_1$ and $s_2$, as FIG. 3 illustrates.

Of course, in everything above, the denominator $H_{11}(\omega)H_{22}(\omega)-H_{12}(\omega)H_{21}(\omega)$ must not be cancelled for any pulsation values $\omega$ in the vibration frequency range. If that were the case, the observability condition would not be verified. It would not be possible to deduce the excitations from the kinematic measurements, and it would be necessary to position the kinematic sensors differently.

The calculation above is only one illustration of how to develop a state observer for a mechanical stress at a critical point. It can immediately be applied to a single sensor or to a number of sensors greater than two, always subject to observability, therefore subject to the number of measurement possibilities being at least equal to the number of degrees of freedom of the excitations.

The finite element calculation is based on networking the geometrical structure for the electronic assembly in polyhedral elements and on writing mechanical vibration equations based on the Galerkin method, also called weak formulation. The finite element method is abundantly documented in applied mathematics and mechanics journals. The calculation can be performed with one of the many software packages on the market. An overview of this technique is available in an article titled, "Durability Modelling of a BGA Component under Random Vibration", presented at the EuroSimE Conference in Freiburg-im-Breisgau on Apr. 21-23, 2008, and available on the website http://ieeexplore.ieee.org/stamp/stamp.jsp?arnumber=4525047&isnumber=4525005.

The damage calculation 5 can be performed for example according to the well-known (NF-A03-406) rainflow method when the mechanical stress evaluated by the state observer is scalar. In this method, all of the local extrema for the mechanical stress are identified, and an algorithm can identify the mechanical stress cycles, each cycle being defined by one of the local minima and by one of the local maxima for the mechanical stress. Each cycle contributes to the damage at critical point 0. An example of a cumulative damage calculation consists of using the Palmgren-Miner hypothesis, according to which the cumulative damage is a scalar dimension incrementing by a value at each cycle that depends only on characteristics of the considered cycle, independently of the preceding cycles. When the damage expects a threshold value, we can consider that a failure at critical point 0 has a significant likelihood of occurrence, and the monitoring device is then capable of generating an alarm. Then, preventative measures can be taken before the considered failure occurs.

When the mechanical stress is more generally tensorial, there are several methods. One is presented in the "Durability Modelling of a BGA Component under Random Vibration" article mentioned above. Otherwise, there are also general rainflow methods using tensorial dimensions. Finally, we can cite the multi-axial criteria of Dang Van and de Sines. See "Mécanique des matériaux solides", J. Lemaître, J.-L Chaboche, ISBN 2-10-001397-1.

The invention claimed is:

1. A method of evaluating the vibration fatigue ageing of an electronic assembly, comprising the steps of:
   measuring one or more kinematic dimensions at one or more specific points subject to vibratory movement to provide kinematic measurements;
   establishing a dynamic model based on the kinematic measurements and mechanical stress suffered at critical points with regard to vibration fatigue, said dynamic model being referred to as a state observer; and
   calculating mechanical stress based on the state observer to ascertain a damage condition for each of the critical points to provide damage state calculations, wherein damage conditions are used to determine ageing of the electronic assembly; and wherein the kinematic measurements, the state observer, and the damage state calculations are included in an embedded device having an autonomous calculation capacity.

2. The method of claim 1, wherein an electronic assembly is an electronic card.

3. The method of claim 1, wherein the step of measuring comprises the step of measuring acceleration at said one or more specific points subject to vibratory movement.

4. The method of claims 1, wherein the step of measuring comprises the step of measuring stress at said one or more specific points subject to vibratory movement.

5. The method of claim 1, wherein said one or more specific points are locations of attachments to one or more holders.

6. The method of claim 1, comprising the step placing a kinematic sensor at a location on the electronic assembly that is neither an attachment of the electronic assembly to a holder nor a critical point to be monitored.

7. The method of claim 1, further comprising the step of calculating a state of the state observer using a finite element method.

8. The method of claim 1, further comprising the step of placing one or more sensors at one or more locations that allow for observability of the mechanical stress at the critical points based on a vibratory analysis of the electronic assembly by means of a finite element method.

9. The method of claim 1, wherein the number of measurement points is greater than or equal to the number of degrees of freedom of excitations.

\* \* \* \* \*